United States Patent [19]
Sato et al.

[11] Patent Number: 5,235,058
[45] Date of Patent: Aug. 10, 1993

[54] 3(5)-HYDRAZINOPYRAZOLE COMPOUNDS

[75] Inventors: Tadahisa Sato; Keizo Kumura, both of Minami-ashigara, Japan

[73] Assignee: Fuji Photo Film Co., Ltd., Kanagawa, Japan

[21] Appl. No.: 760,926

[22] Filed: Sep. 17, 1991

[30] Foreign Application Priority Data

Sep. 20, 1990 [JP] Japan .................................. 2-251610

[51] Int. Cl.$^5$ .................. C07D 231/38; C07D 403/04
[52] U.S. Cl. ............................... 546/279; 548/365.7; 548/312.4; 548/251; 548/257; 548/260; 548/261; 548/262.4; 548/266.2; 548/364.7; 548/369.1; 548/366.1; 548/365.4; 546/193; 546/194; 546/256; 546/271; 546/211; 544/333
[58] Field of Search ............... 548/376, 374, 375, 378, 548/251, 336, 257, 260, 261, 262.4, 266.2; 546/193, 194, 256, 271, 279, 211; 544/333

[56] References Cited

PUBLICATIONS

Chemical Abstracts, "Preparation of 5-(acyl)hydrazinopyrazole-4-carboxylate esters as intermediates for photographic magenta couplers", vol. 110, No. 5, Jan. 1989. abstract No. 38989g.

Chemical Abstracts, "Preparation of 5-hydrazino-1-H-pyrazoles as intermediates for 1H-pyrazolo(3,2-c)-s-triazole couplers for photography", vol. 109, No. 25, Dec. 1988. abstract No. 231006s.

Chemical Abstracts, "Preparation of 5-hydrazino-1-H-pyrazoles as intermediates for magenta couplers", vol. 109, No. 21, Nov. 1988. abstract No. 190409e.

*Primary Examiner*—C. Warren Ivy
*Assistant Examiner*—Zinna N. Davis
*Attorney, Agent, or Firm*—Burns, Doane, Swecker & Mathis

[57] ABSTRACT

There is disclosed a 3(5)-hydrazinopyrazole compound represented by the following formula (I):

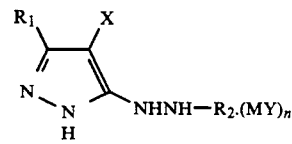

wherein $R_1$ represents a hydrogen atom, an alkyl group, an aryl group, a heterocyclic group, a hydroxyl group, an alkoxy group, or an aryloxy group, $R_2$ represents a hydrogen atom or an acyl group, X represents an aryloxy group, an alkoxy group, a heterocyclic oxy group, or an azolyl group, M represents a hydrogen ion or a metal ion, Y represents an acid radical, and n is 0 or a positive number.

15 Claims, No Drawings

3(5)-HYDRAZINOPYRAZOLE COMPOUNDS

FIELD OF THE INVENTION

The present invention relates to a novel 3(5)-hydrazinopyrazole compound that is an intermediate for synthesizing 1H-pyrazolo[5,1-c][1,2,4]triazoles having an aryloxy group, an alkoxy group, a heterocyclic oxy group, or an azolyl group at the 7-position, and which are useful as a coupler for silver halide color photographic materials.

BACKGROUND OF THE INVENTION 1H-pyrazolo[5,1-c][1,2,4]triazole (named in accordance with the IUPAC nomenclature, and also sometimes called 1H-pyrazolo[3,2-c]-s-triazole) compounds are compounds useful as couplers, particularly as magenta couplers, for photographic materials and are described, for example, in British Patent No. 1,252,418, U.S. Pat. No. 3,725,067, and Journal of the Chemical Society, Parkin I, 2047 (1977).

Early processes for the preparation of these compounds are described in the above-mentioned patents and literature and Research Disclosure, Vol. 124, No. 12443 (1977). Typical processes thereof can be illustrated by the following reaction schemes:

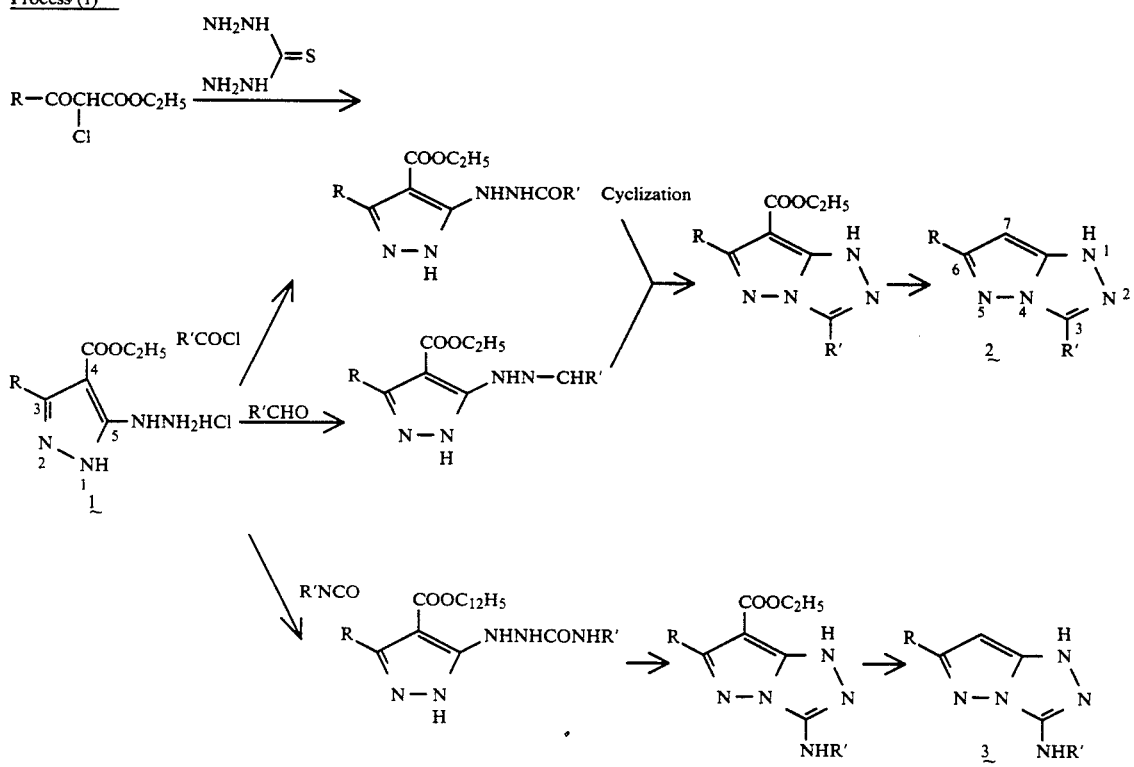

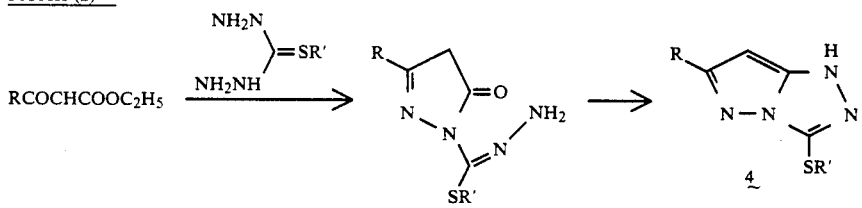

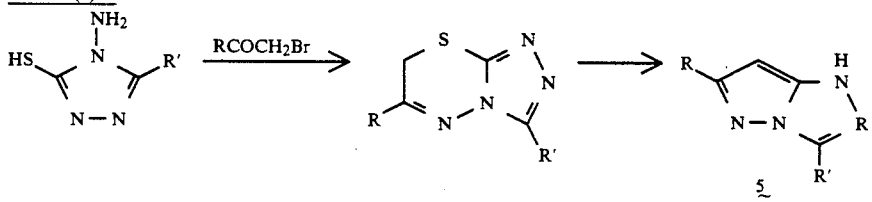

In the above early synthesis processes, R was limited to an alkyl group, an aryl group, or a heterocyclic group, and there was a restriction that the process could only be carried out by synthesizing first a coupler whose 7-position is unsubstituted (it is called a four-equivalent coupler) like 2, 3, 4, and 5 and by then synthesizing a coupler having a coupling releasing group (a group or an atom capable of being released upon a coupling reaction) (it is called a two-equivalent coupler).

As a measure to solve the problems, or limitations for production, a method wherein a halogen is introduced previously in the 4-position, to synthesize a hydrazinopyrazole (the substituent corresponding to —COOC$_2$H$_5$ of compound 4 is a halogen atom), and then a two-equivalent coupler is synthesized based on the above-mentioned process (1), is disclosed in JP-A ("JP-A" means unexamined published Japanese patent application) No. 249987/1986, although the method is applied only to a case wherein the coupling releasing group is a halogen. Compounds capable of being used in the method are disclosed, for example, in JP-A Nos. 249967/1986, 249968/1986, 249969/1986, 158260/1987, 195366/1987, 195367/1987, and 228066/1987. Owing to these patents, it has become possible to synthesize couplers wherein R can be replaced with various substituents and a halogen atom is introduced as a coupling releasing group a reaction by way of not forming a four-equivalent coupler. However, if a coupling releasing group other than halogen is to be introduced, there is still a problem that further steps are required.

As methods for introducing, in the 7-position of 1H-pyrazolo[5,1-c][1,2,4]triazole coupler, a group, besides a halogen, that is a coupling releasing group, a synthesis method, which is of an aryloxy releasable type, is disclosed in JP-B ("JP-B" means examined Japanese patent publication) No. 27411/1972, and a synthesis method, which is of a nitrogen atom releasable type, is disclosed in JP-A No. 99437/1984, but they are synthesis methods wherein four-equivalent couplers or halogen (bromine) atom releasable two-equivalent couplers are involved and their yields are unsatisfactory.

When a coupler is introduced in a photographic system, the choice of the coupling releasing group is quite important to control the color-forming property and to improve the stability. Among couplers, two-equivalent 1H-pyrazolo[5,1-c][1,2,4]triazole magenta couplers, wherein the coupling releasing group is an aryloxy group, an alkoxy group, a heterocyclic oxy group, or an azolyl group, have such advantages that (1) their activity is high and (2) yellow stain does not occur even when processed with a stabilizing bath containing formalin, in comparison with couplers wherein the coupling releasing group is a halogen atom, and therefore the former are more useful than the latter wherein the coupling releasing group is a halogen atom. However, such two-equivalent couplers have the above-mentioned problems involved in their synthesis and they are not suitable to be produced industrially.

This is mainly because there has not been a suitable synthesis process or a proper intermediate to be used therein for synthesizing 1H-pyrazolo[5,1-c][1,2,4]triazoles that have such a group capable of being released upon coupling reaction.

SUMMARY OF THE INVENTION

Therefore, the object of the present invention is to provide an intermediate useful for synthesizing a 1H-pyrazolo[5,1-c][1,2,4]-triazole coupler that has in the 7-position a group capable of being released upon a coupling reaction.

The above and other objects, features, and advantages of the invention will become fully apparent in the following description.

DETAILED DESCRIPTION OF THE INVENTION

The inventors have studied in various ways to attain the object and have found that by a process completely different from the synthesis process, wherein a halogen atom is a coupling releasing group, a novel pyrazole compound having a group corresponding to the above specific coupling releasing group can be synthesized, and that the novel pyrazole compound is quite suitable as an intermediate for synthesizing the above 1H-pyrazolo[5,1-c][1,2,4]triazole coupler, leading to this invention.

The present invention provides a novel 3(5)-hydrazinopyrazole compound represented by the following formula (I):

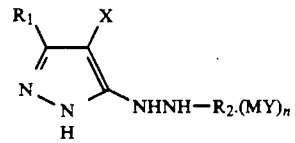

wherein $R_1$ represents a hydrogen atom, an alkyl group, an aryl group, a heterocyclic group, a hydroxyl group, an alkoxy group, or an aryloxy group, $R_2$ represents a hydrogen atom or an acyl group, X represents an aryloxy group, an alkoxy group, a heterocyclic oxy group, or an azolyl group, M represents a hydrogen ion or a metal ion, Y represents an acid radical, and n is 0 or a positive number.

The substituents $R_1$, $R_2$, X, M, and Y of the compound of the present invention represented by formula (I) will now be described.

$R_1$ represents a hydrogen atom, an alkyl group, an aryl group, a heterocyclic group, a hydroxyl group, an alkoxy group, or an aryloxy group, and more particularly the alkyl group represents a linear or branched alkyl, aralkyl, alkenyl, alkynyl, cycloalkyl, or cycloalkenyl group having 1 to 32 carbon atoms, the aryl group represents a phenyl or naphthyl group having 6 to 23 carbon atoms, the heterocyclic group represents a 5- to 7-membered aliphatic or aromatic heterocyclic group, the alkoxy group represents a linear or branched alkoxy group having 1 to 32 carbon atoms, and the aryloxy group represents a phenoxy or naphthoxy group having 6 to 23 carbon atoms, with these groups optionally being further substituted with halogen atoms or organic groups which will be linked through a carbon atom, an oxygen atom, a nitrogen atom, or a sulfur atom. Substituents which may be present on these groups are more particularly, for example, an alkyl group, an aryl group, a heterocyclic group, a cyano group, an acyl group, an aryloxycarbonyl group, an alkoxycarbonyl group, a carbamoyl group, an alkoxy group, an aryloxy group, a heterocyclic oxy group, an acyloxy group, a carbamoyloxy group, a silyloxy group, an aryloxycarbonylamino group, an acylamino group, an anilino group, a ureido group, a sulfamoylamino group, an alkoxycarbonylamino group, a sulfonamido group, an aryloxycarbonylamino group, an imido group, an alkylthio group, an arylthio group, a heterocyclic thio group, a sulfamoyl group, a sulfonyl group, a sulfinyl group, a fluorine atom, a chlorine atom, and a bromine atom. More particularly, $R_1$ represents an alkyl group such as methyl, ethyl, propyl, isopropyl, n-butyl, t-butyl, cyclopentyl, cyclohexyl, methoxyethyl, ethoxyethyl, t-butoxyethyl, phenoxyethyl, methanesulfonylethyl, 2-hydroxyethyl, (3-pentadecylphenoxy)propyl, 4,4,4-trifluorobutyl, and 3-(2,4-diamylphenoxy)propyl; an aryl such as phenyl, 4-methylphenyl, 4-methoxyphenyl, 4-t-butylphenyl, 2,4-dimethylphenyl, 4-methoxyphenyl, 4-tetradecaneamidophenyl, 2-methoxyphenyl, 2-acetamidophenyl, 1-naphthyl, and 2-naphthyl; a heterocyclic group such as 2-tetrahydrofuranyl, 2-tetrahydrothienyl, 1-piperidino, 4-pyridyl, 1-pyrazolyl, 2-furyl, 2-thienyl, 2-pyrimidinyl, and 2-benzothiazolyl; a hydroxyl group; an alkoxy group such as methoxy, ethoxy, isopropoxy, n-butyloxy, t-butyloxy, 2-methoxyethoxy, 2-ethoxyethoxy, 2-dodecyloxyethoxy, 2-phenoxyethoxy, 2-(4-t-amylphenoxy)ethoxy, 2-(4-nitrophenoxy)ethoxy, and 2-(2,4-dichlorophenoxy)ethoxy; or an aryloxy group such as phenoxy, 2-methoxyphenoxy, 2-methylphenoxy, 3-methoxyphenoxy, 3-methylphenoxy, 4-methoxyphenoxy, 4-methylphenoxy, 2,4-dimethoxyphenoxy, 2,4-dimethylphenoxy, 4-methoxycarbonylphenoxy, 1-naphthyloxy, 2-naphthyloxy, 1-methoxy-2-naphthyloxy, 2-methoxy-1-naphthyloxy, and 4-methoxy-1-naphthyloxy.

$R_1$ represents preferably an alkyl group, an aryl group, or an aryloxy group with an alkyl group more preferred. The alkyl group is preferably methyl, ethyl, isopropyl, or t-butyl, and more preferably ethyl and isopropyl group with an ethyl group most preferred.

$R_2$ represents a hydrogen atom or an acyl group and more particularly the acyl group is a substituted or unsubstituted alkanoyl or aryloyl group. These acyl groups may further have substituents that can be possessed by $R_1$ as mentioned above. More particularly the substituted or unsubstituted alkanoyl group includes acetyl, propionyl, octanoyl, palmitoyl, 3-(4-nitrophenyl)butanoyl, 2-phthalimidoethanoyl, 3-phthalimidopropanoyl, 2-phthalimidopropanoyl, 2-(2-phenoxy-4-nitrobenzene-sulfonamido)ethanoyl, 2-[2-phenoxy-5-{2-(4-methoxyphenoxy)tetradecanoylamino}benzenesulfonamido]ethanoyl, 2-[2-phenoxy-5-{2-(3-t-butyl-4-methoxyphenoxy) tetradecanoylamino}benzenesulfonamido]ethanoyl, and 2-(2-octyloxy-5-t-octylbenzenesulfonamido) propanoyl, and the substituted or unsubstituted aryloyl group includes benzoyl, 4-dodecyloxybenzoyl, 2-octadecyloxybenzoyl, 2-methoxy-5-nitrobenzoyl, 2-chloro-4-nitrobenzoyl, 4-octadecyloxybenzoyl, 2-chloro-5-palmitoylaminobenzoyl, and 2,4,6-trimethylbenzoyl.

Preferably, $R_2$ represents a hydrogen atom, 3-(4-nitrophenyl)butanoyl, 2-phthalimidoethanoyl, 3-phthalimidopropanoyl, 2-phthalimidopropanoyl, 2-(2-phenoxy-4-nitrobenzenesulfonamido)ethanoyl, 2-[2-phenoxy-5-{2-(4-methoxy-phenoxy)tetradecanoylamido}benzenesulfonamido]ethanoyl, or 2-[2-phenoxy-5-{2-(4-methoxyphenoxy) tetradecanoylamino}benzenesulfonamido]ethanoyl, 2-(2-octylbenzenesulfonamide)propanoyl with a hydrogen atom particularly preferred.

X represents an aryloxy group (preferably having 6 to 25 carbon atoms), an alkoxy group (preferably having 1 to 5 carbon atoms), a heterocyclic oxy group (preferably a 5- to 7-membered cyclic group whose hetero atom is selected from N, O, S, and Se), or an azolyl group (preferably whose other hetero atom is N, O, S, or Se). These groups may further have substituents that can be possessed by $R_1$ as mentioned above. More particularly, X represents an aryloxy group such as phenoxy, 4-methylphenoxy, 2,4-dimethylphenoxy, 4-t-octylphenoxy, 4-nonylphenoxy, 4-methoxycarbonylphenoxy, 4-(4-benzyloxyphenylsulfonyl)phenoxy, 4-cyanophenoxy, 4-methoxyphenoxy, 1-naphthyloxy, and 2-naphthyloxy, an alkoxy group such as methoxy, methoxymethoxy, ethoxymethoxy, 2-ethoxyethoxy, 2-phenoxyethoxy, 2-methanesulfonylethoxy, 2-methylthioethoxy, 2-phenylsulfonylethoxy, and 2-(4-carboxyphenoxy)ethoxy, a heterocyclic oxy group such as 2-pyridyloxy, 4-pyridyloxy, 1-phenyltetrazole-5-oxy, and 2-tetrahydropyranyloxy, or an azolyl group such as 1-pyrazolyl, 1-imidazolyl, 3-chloropyrazol-1-yl, 3-nitropyrazol-1-yl, 3-cyanopyrazol-1-yl, 3-methoxycarbonylpyrazol-1-yl, 3-methylpyrazol-1-yl, 3,5-dimethylpyrazol-1-yl, 1-triazolyl, and 1-benzotriazolyl.

Preferably X represents an aryloxy group such as 4-methylphenoxy, 4-methoxycarbonylphenoxy, and 4-(4-benzyloxyphenylsulfonyl) phenoxy, an alkoxy group such as methoxymethoxy, ethoxyethoxy, and 2-methanesulfonylethoxy, a heterocyclic oxy group such as 2-pyridyloxy, or an azolyl group such as 1-pyrazolyl, 4-chloropyrazole-1-yl, and 4-methoxycarbonylpyrazole-1-yl.

M represents a hydrogen ion or a metal ion. The metal ion represents an ion, for example, of Sn, Fe, Zn, Ti, Ni, or Cr, and preferably an ion of Sn, Fe, or Zn. Particularly preferably M represents a hydrogen ion or an ion of Sn.

Y represents an acid radical, for example, an inorganic acid radical such as $Cl^\ominus$, $Br^\ominus$, $I^\ominus$, $HSO_4^\ominus$, $SO_4^{2\ominus}$, and $ClO_4^\ominus$, or an organic acid radical such as $CH_3SO_3^\ominus$, $CF_3SO_3^\ominus$, $C_6H_5SO_3^\ominus$, $CH_3C_6H_4SO_3^\ominus$, $CH_3COO^\ominus$, $CF_3COO^\ominus$, and $C_6H_5COO^\ominus$. Among them, $Cl^\ominus$, $Br^\ominus$, $HSO_4^\ominus$, $SO_4^{2\ominus}$, $CH_3SO_3^\ominus$, and $CH_3COO^\ominus$ are preferred, with $Cl^\ominus$ particularly preferred. The number of Y is determined by the oxidation numbers of M and therefore the number of Y is not necessarily 1 if M is a metal atom. That is, MY takes, for example, the form of $SnCl_4$, $FeCl_3$, $ZnCl_2$, $Sn(SO_4)_2$, or $Fe_2(SO_4)_3$.

n is 0 or a positive number and is not necessarily a natural number. If M is a hydrogen ion, n is a positive number of 0 to 4, preferably a positive number of 0 to 2. If M is a metal ion, n is a positive number of 0 to 1, preferably a positive number of 0 to ½.

Specific examples of the 3(5)-hydrazinopyrazole compounds represented by formula (I) of the present invention are shown below, but the present invention is not restricted to them (the following compounds are separated in the forms of acid salts and metal complexes in many cases, but since the number represented by n is not determined simply, structures only in the free forms are shown here).

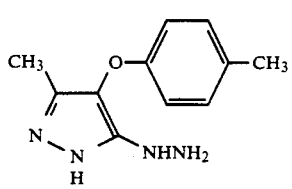

(1)

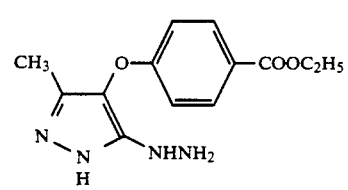

(2)

-continued

-continued
(19)
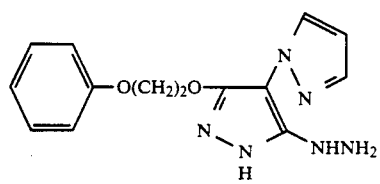
(20)
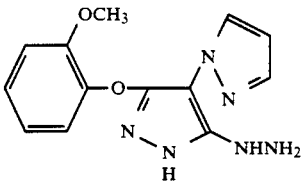
(21)
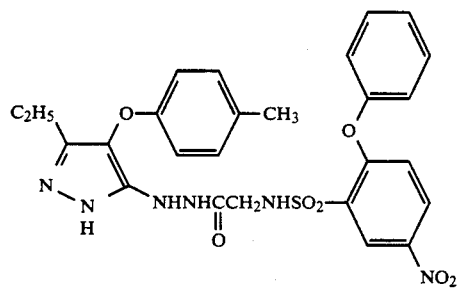
(22)
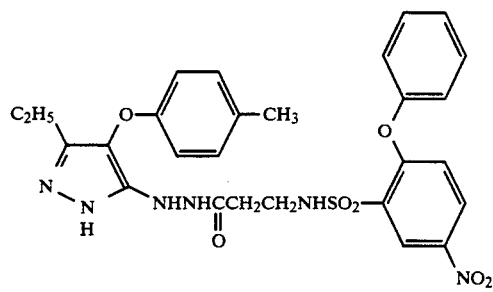
(23)
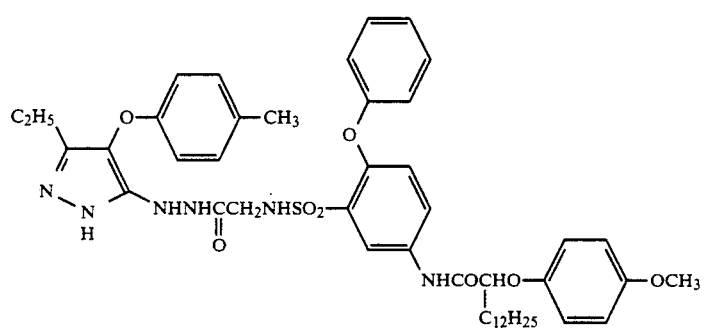
(24)
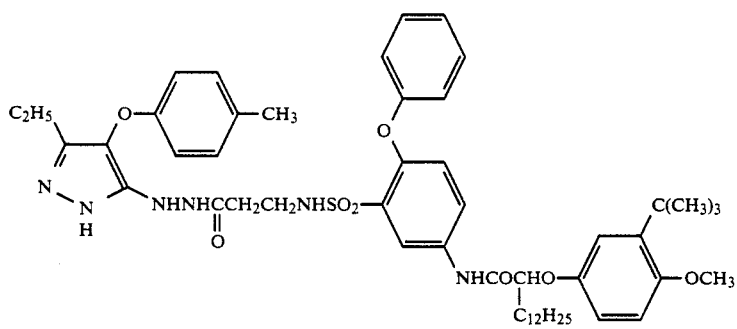
(25)
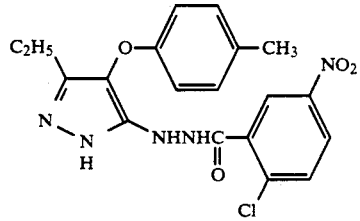
(26)
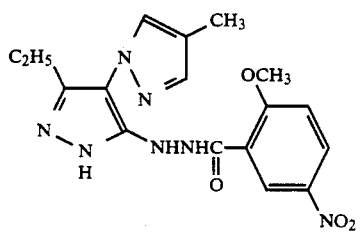
(27)
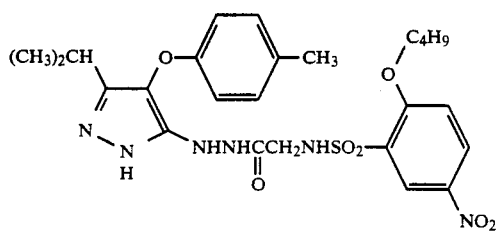
(28)
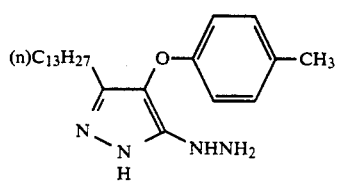

-continued

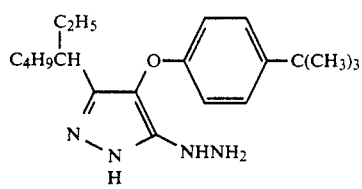

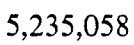
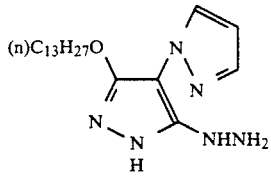

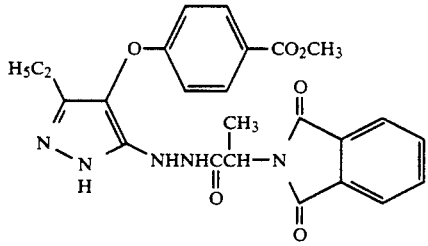

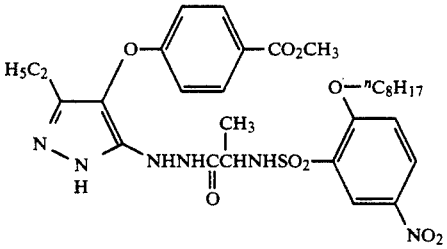

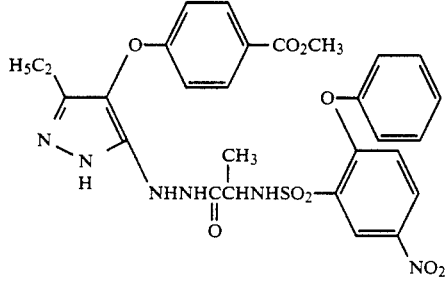

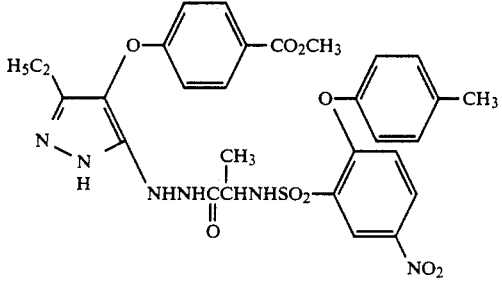

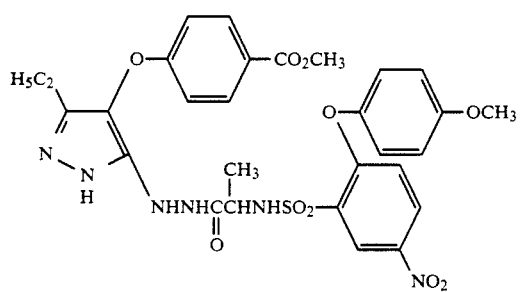

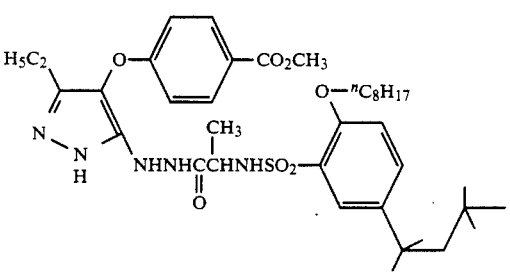

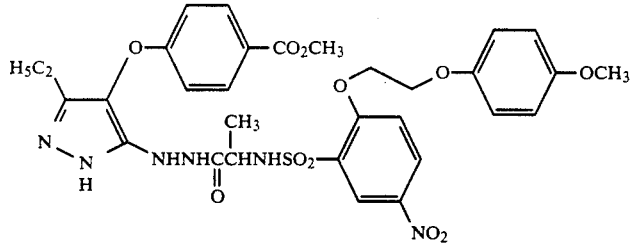

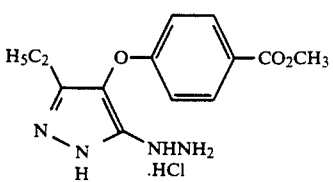

As described above, when $R_2$ of the compound of the present invention represents a hydrogen atom, the compounds are separated in the forms of acid salts or metal complexes in many cases. For example, the following compound (38) can be mentioned:

The method of synthesis of compound according to the present invention will be described below.

The method of synthesis is represented roughly by the following (Scheme 1).

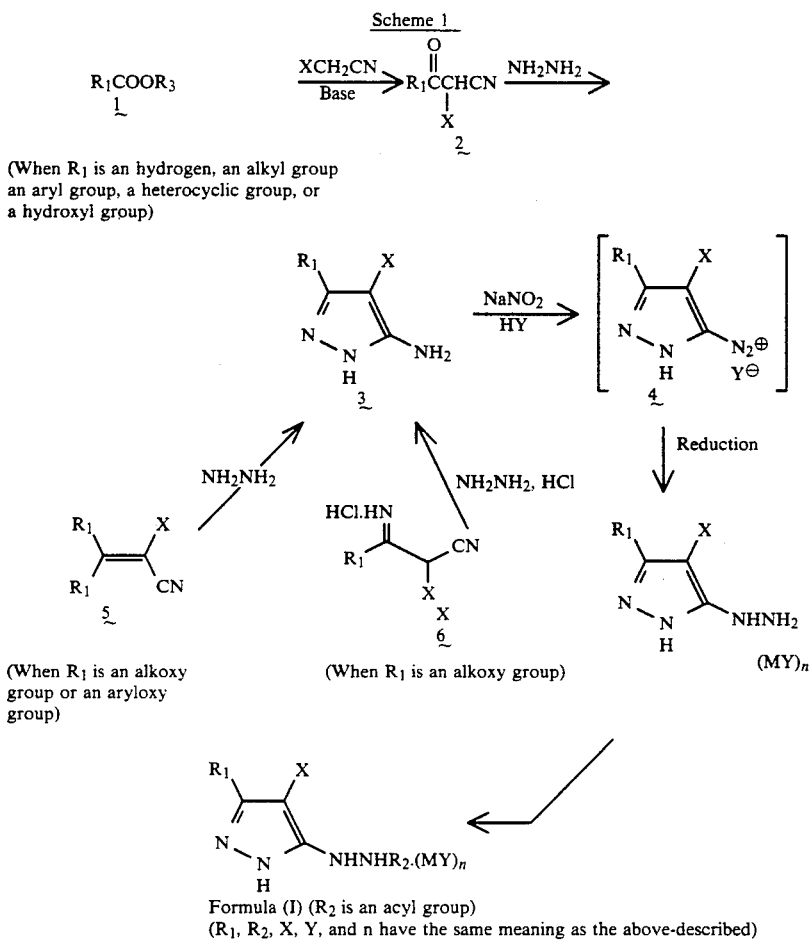

Scheme 1

(When $R_1$ is an hydrogen, an alkyl group an aryl group, a heterocyclic group, or a hydroxyl group)

(When $R_1$ is an alkoxy group or an aryloxy group)

(When $R_1$ is an alkoxy group)

Formula (I) ($R_2$ is an acyl group)
($R_1$, $R_2$, X, Y, and n have the same meaning as the above-described)

In the above scheme 1, the synthesis of the compound represented by formula (I) ($R_2$ =H) through 3 to 4 is carried out as follows. 3 is dissolved or dispersed in an aqueous solution of HY (generally use is made of a concentrated hydrochloric acid of Y =Cl). The molar ratio of the acid in the aqueous solution to 3 is adjusted to 2 to 20, preferably to 5 to 15. Acetic acid may be used as a co-solvent. An aqueous solution containing 1 to 1.5 equivalents, preferably 1 to 1.2 equivalents, of sodium sulfite is added dropwise thereto and the reaction temperature is about 0° to about 30° C., preferably about 5° to about 20° C. The reaction time is from 10 min to 2 hours, preferably from 20 min to 1 hour. The aqueous solution of 4 thus obtained is reacted with a reducing agent to drive a compound represented by formula (I) ($R_2$ =H), the reducing agent being a sulfite or a reducing metal or metal salt, preferably a sulfite or a stannous halide. Reduction with a stannous halide is carried out in such a way that the reaction liquid of 4 is added dropwise at a temperature of about 0° to about 30° C., preferably about 5° to about 25° C., to the concentrated aqueous solution of HY in which the reducing agent has been dissolved. The reaction time is from 20 min to 2 hours, preferably from 30 min to 1 hour. Although reversed dropping is possible, secondary reactions increase in some cases. The amount of the stannous halide to be used for 3 is 1.9 to 3 mol equivalents, preferably 2 to 2.3 mol equivalents. The amount of the aqueous acid solution in which the reducing agent is to be dissolved is preferably such that the reducing agent is just dissolved. In some cases, the compound represented by formula (I) ($R_2$ =H) is deposited from a reaction liquid when it is in the form of a tin complex or acid salt, and in that case, after filtration, washing with a solvent that will not dissolve the tin complex or acid salt (in many cases acetonitrile is preferable) is carried out, followed by drying, to obtain the tin complex or acid salt. The purity is determined by NMR using an internal standard. If the compound is to be converted to its acid salt or metal complex, the compound is once made into a free form and reaction with an acid or metal complex is carried out. Acylation of the compound of formula (I) ($R_2$ =H) can be carried out using an acid chloride, an acid anhydride, a mixed acid anhydride (synthesized, for example using ROCOCl and t-BuCOCl), or a carboxylic acid and DCC. In that case, suitably a base is used, and a preferable base is trialkylamine.

The amount of the acylating agent used here is 0.5 to 1.5 equivalents, preferably 0.8 to 1.2 equivalents, to the hydrazine compound and if the hydrazine compound, is an acid salt or a metal complex, the amount of the base to be used is the amount required to neutralize it plus 0.7 to 2.0 equivalents, preferably 0.9 to 1.5 equivalents. The reaction temperature is about 0° to about 100° C., preferably about 5° to about 60° C. If the temperature is to be raised over room temperature, the temperature is preferably raised gradually after the addition of the acylating agent. The reaction time is from 10 min to 3 hours, preferably from 30 min to 2 hours. The acylated compound can be purified by recrystallization or column chromatography.

The synthesis of 3 through 1 and 2 can be carried out based on the processes described in JP-A 6274/1989 and Japanese Patent Application No. 117852/1989.

The synthesis of 3 from 5 can be carried out based on the processes described in JP-A Nos. 47769/1989 and 47770/1989.

The synthesis of 3 from 6 can be carried out based on the process described in JP-A No.13072/1989.

By using the present 3(5)-hydrazinopyrazole compound, a 1H-pyrazolo[5,1-c][1,2,4]triazole coupler, wherein an aryloxy group, an alkoxy group, a heterocyclic oxy group, and an azolyl group can be a group capable of being released, can be synthesized directly, so that the process for the preparation can be shortened. Therefore, by using this compound, the coupler can be produced inexpensively and easily on an industrial scale.

The synthesis processes will now be described in detail based on Examples.

EXAMPLE 1

Synthesis of Exemplified Compound (5)

200 g (0.92 mol) of 5-amino-3-ethyl-4-(4-methylphenoxy)1H-pyrazole was added to 768 ml of concentrated hydrochloric acid (12N, 9.2 mol) and the mixture was stirred while being cooled with ice. A solution of 70 g of sodium nitrite in 120 ml of water was added thereto dropwise. During the addition the internal temperature was kept at 15° C. or below. After the addition the reaction liquid was stirred for about 30 min while being cooled with ice, and the obtained orange reaction liquid was added dropwise to 384 g (2.0 mol) of stannous chloride dissolved in 800 ml of concentrated hydrochloric acid while being cooled with ice. After the addition stirring was effected for 30 min and the deposited white crystals were filtered under suction and then washed with concentrated hydrochloric acid. The obtained wet crystals were transferred to a beaker, 1 liter of acetonitrile was added thereto followed by stirring, and the crystals were filtered under suction and were washed with acetonitrile. The obtained pale yellow crystals were dried in a desiccator containing $P_2O_5$ under reduced pressure by an aspirator, to obtain the complex salt of Exemplified compound (5) with tin chloride. Yield: 251 g. Melting point: 144° to 148° C.

NMR (200 MHz, DMSO-$d_6$): $\delta$, 3.40 (3H, S), 6.1 (2H, brs), 6.78 (2H, d, J=11.0 Hz), 7.11 (2H, d, J=11.0 Hz), 10.0 (2H, brs).

The purity was determined by using ethylene glycol as an internal standard; the content of (5) was found to be 64.1 wt. %. That approximately corresponds theoretically to the content of the case wherein stannic chloride ($SnCl_4$) and (5) form a complex of 1:2. Based on the content, it was calculated that the yield was 79.4%.

EXAMPLE 2

Synthesis of Exemplified Compound (6)

96.6 g of 5-amino-3-ethyl-4-(4-methoxycarbonyl-phenoxy)-1H-pyrazole was added to 258 ml of concentrated hydrochloric acid and the mixture was stirred while being cooled with ice. A solution of 24.4 g of sodium nitrite in 43 ml of water was added dropwise thereto while the internal temperature was kept at 8° C. or below, and then the mixture was stirred for 30 min while the internal temperature was kept at 8° C. or below. Separately, a solution of 139 g of stannous chloride in 258 ml of concentrated hydrochloric acid was prepared, and it was added to the previous reaction mixture while the temperature was kept at 10° C. or below with ice-cooling. Thereafter the reaction mixture was stirred for 1 hour while the internal temperature was kept at 10° C. or below. 700 ml of ethyl acetate was added thereto, to carry out the extraction, and the thus formed ethyl acetate layer was washed twice with 400 ml of a solution saturated with sodium chloride. Then, after the ethyl acetate layer was dried with anhydrous sodium sulfate and concentrated in a rotary evaporator, 200 ml of ethyl acetate was added to the thus obtained residue, to dissolve it. 100 ml of n-hexane was added to the solution, followed by stirring, and the deposited crystals were filtered, to obtain 105 g of a product having a melting point of 171° to 174° C. A content of 62.99 wt. % of the intended Exemplified compound (6) in the form of the tin chloride complex was found by measurement by NMR.

NMR (200 MHz, DMSO-$d_6$): $\delta$, 9.8 (brs, 4H), 7.95 (d, 2H, J=11.0 Hz), 7.00 (d, 2H, J=11.0 Hz), 3.80 (S, 3H), 2.46 (q, 2H, J=7.0 Hz), 1.07 (t, 3H, J=7.0 Hz).

EXAMPLE 3

Synthesis of Exemplified Compound (7)

100 g of 5-amino-3-ethyl-4-{4-(4-benzyloxyphenylsulfonyl) phenoxy}-1H-pyrazole was added to 800 ml of acetic acid, and while they were stirred, 57.1 ml of concentrated hydrochloric acid was added thereto. A solution of 16.2 g of sodium nitrite in 25 ml of water was added dropwise thereto, while they were cooled with ice and were stirred with the internal temperature kept at 16° C. or below. Thereafter they were stirred for 30 min with the internal temperature kept at 16° C. or below. Separately, a solution of 92.6 g of stannous chloride in 171 ml of concentrated hydrochloric acid was prepared, and the previous reaction liquid was added to it while the internal temperature was kept at 20° C. or below by cooling with ice. After stirring was continued for 1 hour with the internal temperature kept at 20° C. or below, extraction was carried out by adding 500 ml of ethyl acetate. After the ethyl acetate layer was washed three times with 300 ml of water saturated with sodium chloride, it was dried with anhydrous sodium sulfate and was concentrated in a rotary evaporator, to obtain 172.7 g of an oil containing crystals. The oil was subjected to measurement by NMR, and it was found that it contained 27.83 wt. % of the deisired Exemplified compound (7) in the form of a complex of tin chloride. Melting point: 186° to 180° C. (recrystallized from methanol).

NMR (200 MHz, DMSO-$d_6$): $\delta$, 7.0–8.1 (m, 13H), 5.18 (S, 2H), 4.04 (q, 2H, J=7.0 Hz), 1.06 (t, 3H, J=7.0 Hz).

EXAMPLE 4

Synthesis of Exemplified Compound (21)

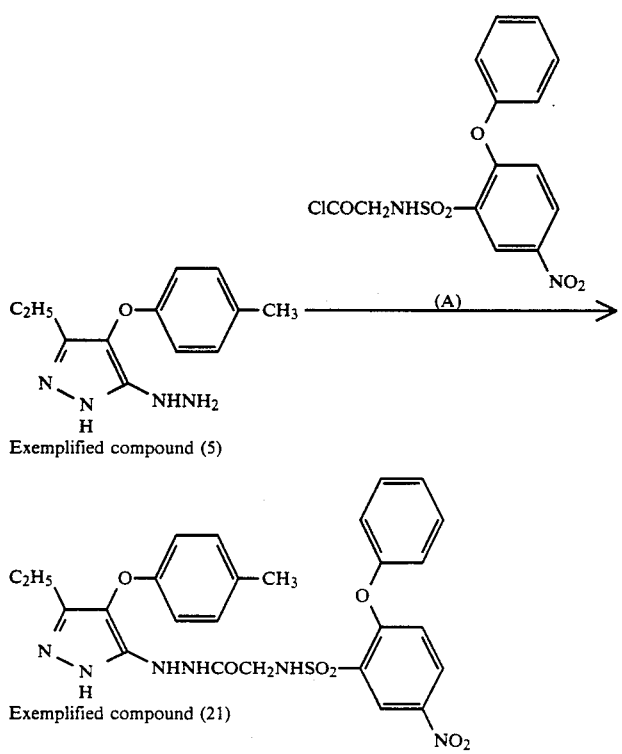

The synthesis of (A) was carried out as follows. First, sodium 2-chloro-4-nitrobenzenesulfonate and phenol were reacted in water in the presence of a base, to obtain sodium 2-phenoxy-4-nitrobenzenesulfonate. This was reacted with $POCl_3/DMAC$ to produce the sulfonyl chloride form, and then the sulfonyl chloride was reacted with the ethyl ester of glycine, to obtain the carboxylic acid ethyl form of (A). Then it was hydrolyzed followed by reaction with $SOCl_2$ in benzene, and then the benzene was distilled off, so that (A) was obtained in the form of crystals.

40 g (0.1 mol) of the thus obtained (A) was dissolved in ethyl acetate, and the solution was added dropwise to a solution of 34 g (0.1 mol) of (5) (64.1%) in a mixed solvent of acetonitrile/dimethylacetamide and 42 ml (0.3 mol) of triethylamine while being cooled with ice. After the addition the temperature was brought to room temperature with stirring, and then heating at 60° C. was effected for about 1 hour. Water was added to the reaction liquid, extraction with ethyl acetate was carried out three times, and the combined ethyl acetate layer was washed with water and then with water saturated with sodium chloride, followed by drying over magnesium acetate. After filtration, when it was condensed in an evaporator, the residue crystallized.

When the crystals were recrystallized from acetonitrile, 34 g (a yield of 60%) of (5) was obtained. Melting point: 177.0° to 180.0° C.

NMR (200 MHz, DMSO-$d_6$): a mixture (about 2:1) of two tautomers; δ, 1.00 (3H, t. J=7.0 Hz), 2.23 (3H, S), 2.32, 2.33 (about 2:1, 2H, q, J=7.0 Hz), 3.55, 3.95 (about 2:1, 2H, d, J=6.5 Hz), 6.65 to 7.60 (10H, m), 7.71, 8.10 (about 1:2, 1H, t, J=6.5 Hz), 8.34, 8.35 (about 2:1, 1H, dd, J=11.0 Hz, 3.0), 8.54, 8.56 (about 1:2, 1H, d, J=3.0 Hz), 9.01, 9.60 (about 1:2, 1H, S).

EXAMPLE 5

Synthesis of Exemplified Compounds (38) and (31)

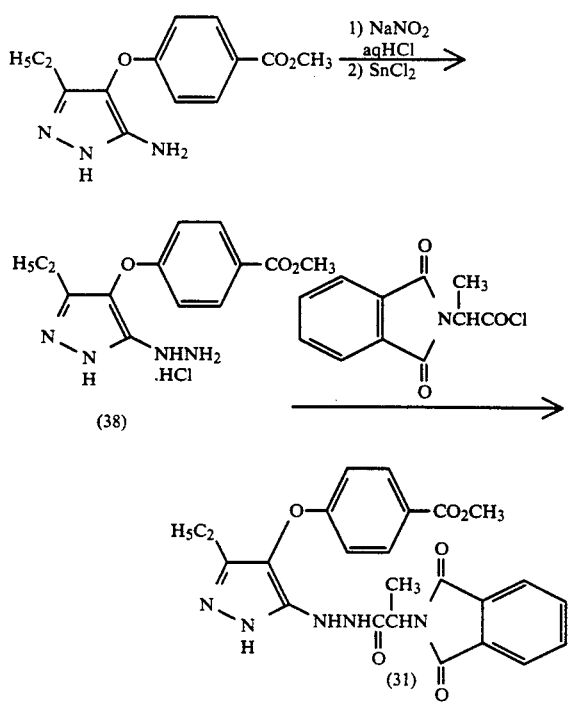

Synthesis of exemplified compound (38)

130.6 g of 5-amino-3-ethyl-4(4-methoxycarbonyl-phenoxy)-1H-pyrazole was added to 386 ml of concentrated hydrochloric acid under keeping the internal temperature at 5° C. or below, while the concentrated hydrochloric acid was being stirred and being cooled in an ice-methanol bath. Then, a solution of 36.2 g of sodium nitrite in 60 ml of water was added thereto dropwise at 5° C. or below of the internal temperature, followed by stirring for 30 minutes at 2° to 5° C. of the internal temperature. The thus-obtained solution of diazonium salt was added to a solution prepared by dissolving 209 g of anhydrous tin (II) chloride in 386 ml of concentrated hydrochloric acid while stirring the solution which was cooled in an ice-methanol bath. At that time, the internal temperature was kept at 5° C. or below. Thereafter the reaction mixture was stirred for 30 min, then 1 liter of ethyl acetate and 1.5 liter of water were added thereto, to carry out the extraction, and the thus formed ethyl acetate layer was washed twice with 1 liter of a saturated sodium chloride solution. Further, an aqueous solution containing 125 of sodium hydrogencarbonate and 125 g of sodium carbonate in 2 liter of water was added to carry out a solution separating operation. The pH of water layer at that time was 8 to 9. The thus obtained ethyl acetate layer was again washed twice with 0.7 liter of a saturated sodium chloride solution, and then dried with anhydrous sodium sulfate. Therafter 27 g of hydrochloric acid gas was blown through the thus obtained ethyl acetate fraction, while the fraction was stirring under ice cooling, at the internal temperature of 27° C. or below, and then precipitated crystal was filtered off and dried to obtain 84.2 g of a product. The product was measured NMR by using ethylene glycol as an internal standard, and it was found that the purity of the desired exemplified compound (38) was 78.14 wt. %. Accordingly, the absolute yield was 42%. Melting point: 102.0° to 105.5° C.

NMR (DMSO-$d_6$): $\delta$=10.0 (brS, 2H), 7.95 (d, 2H, J=9.4 Hz), 7.01 (d, 2H J=9.4 Hz), 6.5 (brs, 3H), 3.83 (S, 3H), 2.45 (q, 2H, J=8.5 Hz), 1.10 (t, 3H, J=8.5 Hz), Synthesis of exemplified compound (31)

To 84.1 g of exemplified compound (38)(78.14 wt. %) 500 ml of acetonitrile was added, and, while the mixture was stirring under cooling in an ice-methanol bath, 117 ml of triethylamine was added dropwise at the internal temperature of 8° C. or below. Therafter to this solution a solution of 47.5 g of 2-phthalimidopropionatechrolide dissolved in 50 ml of N,N-dimethylacetoamide was added dropwise with the internal temperature kept at 3° C. or below. After the addition was completed, the mixture was stirred for 3 hours with the internal temperature kept at 15° C. or below, and then 800 mol of ethyl acetate and 1 liter of water were added thereto to carry out an extraction. The thus obtained ethyl acetate layer was washed 3 times with a mixture of 500 ml of water and 250 ml of a saturated sodium chloride solution. Then, after the ethyl acetate layer was dried with anhydrous sodium sulfate and concentrated in a rotary evaporator, the thus obtained residue was purified by a silica gel column chromatography to obtain 82.1 g (yield 86%) of desired exemplified compound (31) as an oil.

NMR (DMSO-$d_6$): $\delta$=9.37 (s, 1H), 7.93 (d, 2H, J=8.0 Hz), 7.5 to 7.8 (m, 4H), 6.93 (d, 2H J=8.0 Hz), 6.6 (brs, 1H), 4.86 (q, 1H, J=7.1 Hz), 3.87 (S, 3H), 2.36 (q, 2H, J=7.6 Hz), 1.58 (d, 3H, J=7.1 Hz), 1.03 (t, 3H, J=7.6 Hz)

Other Exemplified Compounds were synthesized in accordance with the processes shown in Examples 1 to 4. Their melting points are given below.

| Exemplified Compound | Melting Point (°C.) |
|---|---|
| (1) | 150–153 |
| (2) | 179–182 |
| (3) | 140–142 |
| (4) | 132–135 |
| (8) | 125–127 |
| (9) | 130–136 |
| (10) | 175–177 |
| (11) | 160–165 |
| (12) | 140–143 |
| (13) | 135–137 |
| (14) | 110–115 |
| (15) | 153–158 |
| (16) | 95–99 |
| (17) | 165–168 |
| (18) | 180–182 |
| (19) | 175–178 |
| (20) | 170–173 |
| (22) | 165–168 |
| (23) | oil |
| (24) | oil |
| (25) | 176.0–178.0 |
| (26) | 158–162 |
| (27) | 178–181 |
| (28) | 180–185 |
| (29) | 140–145 |
| (30) | 125–130 |
| (31) | oil |
| (32) | oil |
| (33) | 182.0–184.5 |
| (34) | oil |
| (35) | 121.0–124.5 |
| (36) | oil |
| (37) | 196.5–199.0 |
| (38) | 102.0–105.5 |

REFERENCE EXAMPLE

Now, a coupler synthesis example as Reference Example will be given by using a 3(5)-hydrazinopyrazole of the present invention.

Exemplified Compound (21) ⟶

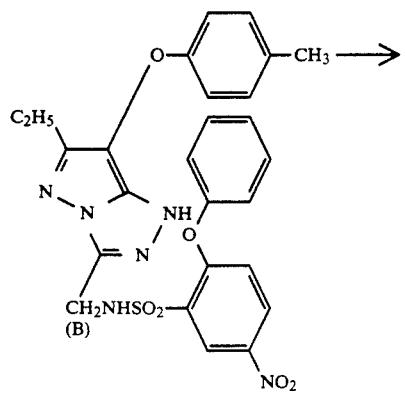

-continued

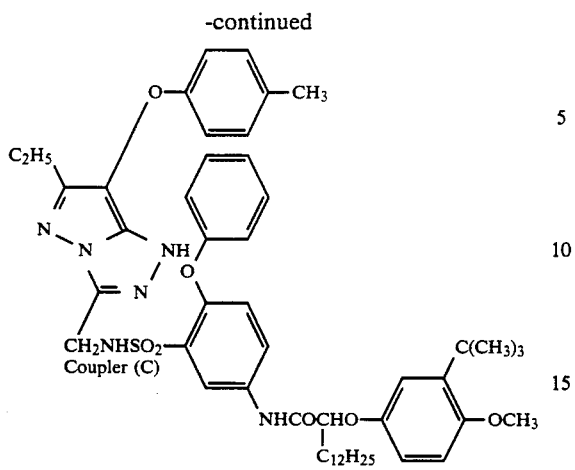

200 ml of acetonitrile was added to 27.2 g (0.048 mol) of (21) and they were stirred under room temperature. 18.5 ml (0.19 mol) of carbon tetrachloride was added thereto, and then 15.1 g (0.058 mol) of triphenylphosphine was added in three portions over 30 min. The reaction was somewhat exothermic and the reaction liquid gradually became transparent. After stirring for about 1 hour, 1.8 g (0.007 mol) of triphenylphosphine was added and the mixture was allowed to stand overnight. After the mixture was heated for about 2 hours under reflux, the temperature was brought to room temperature, and 16.7 ml (0.12 mol) of triethylamine was added dropwise thereto while being cooled with water, followed by stirring for about 30 min. The reaction liquid was poured into water, extraction with ethyl acetate was effected three times, the combined ethyl acetate layer was treated in a usual manner and then condensed in an evaporator, and the obtained residue was purified by silica gel column chromatography, so that 21.3 g (a yield of 80.9%) of (B) was obtained.

200 ml of methanol, 24.5 g (0.38 mol) of ammonium formate, and 0.6 g of 5% palladium/activated carbon were added to the thus obtained (B), and after the mixture was heated for about 3 hours under reflux, the palladium/activated carbon was removed by filtration, the filtrate was poured to water, extraction with ethyl acetate was carried out three times, and the combined ethyl acetate layer was treated in a usual manner and condensed. The residue was dissolved in acetonitrile, 3.5 ml (0.043 mol) of pyridine was added to the solution, and a solution of 20.2 g (0.043 mol) of 2-(3-t-butyl-4-methoxyphenoxy) tetradecanoyl chloride (90%) in ethyl acetate was added thereto dropwise while being cooled with ice. After the addition, stirring was effected at room temperature for about 1 hour, extraction with ethyl acetate was effected, and purification by silica gel chromatography produced 25 g (a yield of 71%) of Coupler (C). Melting point: 162° to 163° C. (recrystallized from n-hexane containing a little ethyl acetate).

Having described our invention as related to the present embodiments, it is our intention that the invention not be limited by any of the details of the description, unless otherwise specified, but rather be construed broadly within its spirit and scope as set out in the accompanying claims.

What we claim is:

1. A 3(5)-hydrazinopyrazole compound represented by the following formula (I):

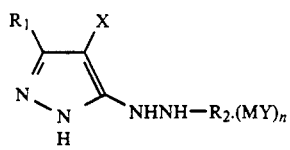

where $R_1$ represents a hydrogen atom, an alkyl group, an aryl group, a member of the group consisting of 2-tetrahydrofuranyl, 2-tetrahydrothienyl, 1-piperidino, 4-pyridyl, 1-pyrazolyl, 2-furyl, 2-thienyl, 2-pyrimidinyl and 2-benzothiazolyl, a hydroxyl group, an alkoxy group, or an aryloxy group, $R_2$ represents a hydrogen atom or an acyl group, X represents an aryloxy group, an alkoxy group, a member of the group consisting of 2-pyridyloxy, 4-pyridyloxy, 1-phenyltetrazole-5-oxy, and 2-tetrahydropyranyloxy, a member of the group consisting of 1-pyrazolyl, 1-imidazolyl, 4-chloropyrazol-1-yl, 3-chloropyrazol-1-yl, 3-nitropyrazol-1-yl, 3-cyanopyrazol-1-yl, 4-methoxycarbonylpyrazol-1-yl, 3-methoxycarbonylpyrazol-1-yl, 3-methylpyrazol-1-yl, 3,5-dimethylpyrazol-1-yl and 1-triazolyl, or 1-benzotriazolyl, M represents a hydrogen ion or a metal ion, Y represents an acid radical, and n is 0 or a positive number.

2. The compound as claimed in claim 1 wherein $R_1$ of formula (I) represents an alkyl group, an aryl group or an aryloxy group.

3. The compound as claimed in claim 1, wherein $R_1$ of formula (I) represents an alkyl group.

4. The compound as claimed in claim 1, wherein $R_1$ of formula (I) is selected from the group consisting of methyl group, ethyl group, isopropyl group, and t-butyl group.

5. The compound as claimed in claim 1, wherein $R_1$ of formula (I) is an ethyl group or an isopropyl group.

6. The compound as claimed in claim 1, wherein $R_2$ of formula (I) represents a hydrogen atom, an alkanoyl group, or an aryloyl group.

7. The compound as claimed in claim 1, wherein $R_2$ of formula (I) represents a hydrogen atom, 3-(4-nitrophenyl) butanoyl, 2-phthalimidoethanoyl, 3-phthalimidopropanoyl, 2-phthalimidopropanoyl, 2-(2-phenoxy-4-nitrobenzenesulfonamido) ethanoyl, 2-[2-phenoxy-5-{2-(4-methoxyphenoxy) tetradecanoylamido}benzenesulfonamido]ethanoyl, or 2-[2-phenoxy-5-{2-(4-methoxyphenoxy)tetradecanoylamino}benzenesulfonamido]ethanoyl or 2-(2-octylbenzene-sulfonamido)propanoyl.

8. The compound as claimed in claim 1, wherein $R_2$ of formula (I) is a hydrogen atom.

9. The compound as claimed in claim 1, wherein X of formula (I) is selected from the group consisting of 4-methylphenoxy, 4-methoxycarbonylphenoxy, 4-(4-benzyloxyphenylsulfonyl) phenoxy, methoxymethoxy, ethoxyethoxy, 2-methanesulfonylethoxy, 2-pyridyloxy, 1-pyrazolyl, 4-chloropyrazol-1-yl, and 4-methoxycarbonylpyrazol-1-yl.

10. The compound as claimed in claim 1, wherein M in formula (I) is selected from the group consisting of ions of hydrogen, Sn, Fe, Zn, Ti, Ni and Cr.

11. The compound as claimed in claim 1, wherein M in formula (I) is selected from the group consisting of ions of hydrogen, Sn, Fe and Zn.

12. The compound as claimed in claim 1, wherein M in formula (I) is a hydrogen ion or an ion of Sn.

13. The compound as claimed in claim 1, wherein Y in formula (I) is selected from the group consisting of $Cl^{\ominus}$, $Br^{\ominus}$, $I^{\ominus}$, $HSO_4^{\ominus}$, $SO_4^{2\ominus}$, $ClO_4^{\ominus}$, $CH_3SO_3^{\ominus}$, $CF_3SO_3^{\ominus}$, $C_6H_5SO_3^{\ominus}$, $CH_3C_6H_4SO_3^{\ominus}$, $CH_3COO^{\ominus}$, $CF_3COO^{\ominus}$, and $C_6H_5COO^{\ominus}$.

14. The compound as claimed in claim 1, wherein Y in formula (I) is selected from the group consisting of $Cl^{\ominus}$, $Br^{\ominus}$, $HSO_4^{\ominus}$, $SO_4^{2\ominus}$, $CH_3SO_3^{\ominus}$, and $CH_3COO^{\ominus}$.

15. The compound as claimed in claim 1, wherein Y in formula (I) is $Cl^{\ominus}$.

* * * * *

UNITED STATES PATENT AND TRADEMARK OFFICE
CERTIFICATE OF CORRECTION

PATENT NO. : 5,235,058
DATED : August 10, 1993
INVENTOR(S) : Sato et al.

It is certified that error appears in the above-identified patent and that said Letters Patent is hereby corrected as shown below:

On the title page, item [75] Inventors: change the last name of the second inventor from "Kumura" to --Kimura--.

Claim 7, line 49, col. 22, "or" should be deleted.

Claim 13, line 3, col. 23, "$Cl^{63}$" should be --$Cl^{\ominus}$--;

line 5, "$C_6H_5COO^{63}$" should be --$C_6H_5COO^{\ominus}$--.

Signed and Sealed this

First Day of November, 1994

Attest:

BRUCE LEHMAN

Attesting Officer

Commissioner of Patents and Trademarks